United States Patent
Weisman et al.

(10) Patent No.: US 6,534,537 B2
(45) Date of Patent: Mar. 18, 2003

(54) USE OF HMG-COA REDUCTASE INHIBITORS TO PREVENT AND TREAT BPH

(76) Inventors: Kenneth Weisman, 30 Springton Pointe Dr., Newtown Square, PA (US) 19073; Michael E. Goldberg, 20 Aspen Dr., Ivyland, PA (US) 18974

( * ) Notice: Subject to any disclaimer, the term of this patent is extended or adjusted under 35 U.S.C. 154(b) by 0 days.

(21) Appl. No.: 09/755,284

(22) Filed: Jan. 5, 2001

(65) Prior Publication Data

US 2002/0004521 A1 Jan. 10, 2002

Related U.S. Application Data

(60) Provisional application No. 60/175,044, filed on Jan. 7, 2000.

(51) Int. Cl.$^7$ .............. A61K 31/40; A61K 31/335; A61K 31/35; A61K 31/235

(52) U.S. Cl. .............. 514/423; 514/452; 514/460; 514/533

(58) Field of Search .............. 514/423, 452, 514/460, 533

(56) References Cited

U.S. PATENT DOCUMENTS 5,605,930 A * 2/1997 Samid .............. 514/510

* cited by examiner

*Primary Examiner*—Frederick Krass
*Assistant Examiner*—Donna Jagoe
(74) *Attorney, Agent, or Firm*—Caesar, Rivise, Bernstein, Cohen & Pokotilow, Ltd.

(57) ABSTRACT

A method of preventing and treating benign prostatic hypertrophy or benign prostatic hyperplasia wherein the method involves administering to a human or an animal a sufficient amount of a HMG Co-A Reductase Inhibitor.

9 Claims, No Drawings

USE OF HMG-COA REDUCTASE INHIBITORS TO PREVENT AND TREAT BPH

This application claims the benefit of the filing date of Jan. 7, 2000 of Provisional Patent Application Ser. No. 60/175,044.

BACKGROUND OF THE INVENTION

Fluvastatin sodium, [R*,S*,-(E)]-(±)-7-[3-(4-fluorophenyl)-1-(1-methylethyl)-H-indol-2-yl]-3,5-dihydroxy-6-heptenoic acid, monosodium salt, empirical formula is C24 H25 FNO4 Na, sold under the trade name of Lescol by Novartis Pharmaceuticals is known as a cholesterol lowering agent which acts as an inhibitor of 3-hydroxy-3-methylglutaryl-coenzyme A (HMG-CoA) reductase.

Cerivastatin sodium, [S-[R*,S*-(E)]-7-[4-(4-fluorophenyl)-5-methoxymethyl)-2,6bis(1-methylethyl)-3-pyridinyl]-3,5-dihydroxy-6-heptenoate, empirical formula C26 H33 F N O5 Na, sold under the trade name Baycol by Bayer Corporation, is incorporated by reference herein, is known as an entirely synthetic, enantiomerically pure inhibitor af HMG-COA reductase.

Atorvastatin Calcium, [R-(R*, R*)]-2-(4-fluorophenyl)-beta, delta-dihydroxy-5-(1-methylethyl)-3-phenyl-4-[(phenylamino)carbonyl]-1H-pyrrole-1-heptanoic acid, calcium salt (2:1) trihydrate, the empirical formula is (C33 H34 F N2 O5)2Ca*3H2O, sold under the trade name Lipitor by Parke-Davis and Pfizer, is known as a synthetic lipid lowering agent inhibiting HMG-CoA reductase.

Lovastatin, {S-[1alpha(R*), 3 alpha, 7 beta, 8 beta (2S*, 4S*), 8a beta]}-1,2,3,7,8,8a-hexahydro-3,7-dimethyl-8-[2-(tetrahydro-4-hydroxy-6-oxo-2H-pyran-2-yl)ethyl]-1-naphthalenyl 2-methylbutanoate, empirical formula C24 H36 O5, sold by Merck & Co. inc under the trade name Mevacor, is known as a cholesterol lowering agent, a metabolite of which inhibits HMG-CoA reductase.

Pravastatin sodium, 1-Naphthalene-heptanoic acid, 1,2,6,7,8,8a-hexahydro-beta, delta,6-trihydroxy-2-methyl-8-(2-methyl-1-oxobutoxy)-, monosodium salt, {1S-[1alpha (betaS*, deltaS*),2 alpha, 6 alpha, 8 beta(R*),8a alpha]}-, sold by Merck and Co. inc under the trade name Pravachol is known as a lipid lowering compound, inhibiting HMG-CoA reductase to reduce cholesterol synthesis.

Simvastatin, chemical name is: butanoic acid, 2,2-dimethyl-1,2,3,7,8,8a-hexahydro-3,7-dimethyl-8-[2-(tetrahydro-4-hydroxy-6-oxo-2H-pyran-2-yl)-ethyl]-1-naphthalenyl ester, {1S-[1alpha,3alpha,7beta,8beta(2S*, 4S*),-8 a beta]}, empirical formula C25 H38 O5, sold by Merck and co. inc under the trade name Zocor, is known as a lipid lowering agent, a metabolite of which inhibits HMG-Co A reductase.

The present invention involves the use of these drugs in the prevention and treatment of benign prostatic hypertrophy.

Recently a higher incidence of Coronary Artery Disease (CAD) was reported in patients with BPH.(1,2) We note that CAD and BPH also share several risk factors; large waist size is a known risk factor for the development of BPH(3), as is a diet high in various lipid sources such as butter, margarine, milk, and beef. A high intake of fruits and vegetables has been found to be protective.(4–6) Risk factors for CAD include a high waist-hip ratio(7), and high lipid intake.(8) BPH and CAD are also similar in that both seem to be modifiable by sex hormones, as the presence of androgen is permissive for the development of BPH, and the natural history of the disease can be modified by certain inhibitors of testosterone metabolism such as finasteride;(9, 10) while CAD can be modified by estrogen in women.(11)

Since BPH and CAD occur together, share risk factors, and can both be modified by sex hormones, we hypothesized that the risk of BPH could be reduced by various HMG Co-A reductase inhibitors which are used to decrease cardiac risk.(12,13)

BPH is difficult to quantify.(14) Recent data demonstrate a log-linear relationship between the volume of BPH and serum concentration of PSA in patients who have no other reason for PSA elevation.(15,16) We reviewed a data base to see if we could demonstrate that the use of HMG Co-A reductase inhibitors was associated with lower prostatic volume as measured by serum PSA levels.

Charts from male patients seen in a urology practice over a 2-year period (1996–1998) were reviewed. Data extracted from patient charts included age, smoking habit, presence of diabetes, and medication history. In addition, history of coronary angioplasty, myocardial infarction (MI), stroke, transient ischemic attack (TIA), parental history for MI, transurethral resection of the prostate (TURP), prostate biopsy, and serum PSA values were obtained.

In order to ensure that serum PSA reflected only the volume of BPH, charts were only abstracted if patients had no conditions, had undergone no procedures, and had been exposed to no drugs known to change PSA values. Patients with a diagnosis of urinary tract infection or prostatitis, a history of various transurethral procedures (i.e. cystoscopy, foley catheter insertion), and prostatic biopsy within 6 months of data collection were not included. Patients with PSA levels of 4.0–10.0 ug/L were included only if prostatic biopsies had been negative. No patient with prostatic carcinoma was included. Patients with PSA values of >10 ug/L were felt to be at increased risk for prostatic carcinoma despite negative biopsies and were not included.(18) Patients were also excluded from analysis if they had taken medications or undergone procedures which could reduce their PSA levels. A history of the use of finasteride resulted in exclusion from the study since this drug can independently reduce PSA levels, as well as independently inhibit or shrink BPH.(9,10,17) No patient who had undergone TURP was included since this procedure can eventually reduce serum PSA concentration.(18) Patients were eliminated from the study if they were younger than 65 years old or older than 80. In the remaining patients, therefore, PSA levels would correlate with volume of BPH. Serum PSA was measured using Microparticle Enzyme Immunoassay (MEIA, Abbott Laboratories).

Descriptive statistics and 95% Confidence Interval (CI) were used to analyze the data.

The charts of 697 male patients were reviewed. 150 met the inclusion-exclusion criteria. Patients were divided into two groups; those on HMG Co-A Reductase inhibitors (statins) (group two) and those with no history of taking statins (group one). Table 1 summarizes the frequency of some of the measured variables between the 2 groups. The data presented demonstrates that the use of statin drugs is associated with a significantly higher fraction of patients with a minimal prostatic volume as determined by PSA values $\leq 1.0$ ug/L. (10.2% vs. 26.2%, 95% CI=0.0154 to 0.305) (table 1).

The use of HMG Co-A Reductase Inhibitors is associated with a higher proportion of elderly men with extremely low prostatic volumes. These drugs have utility in preventing and treating benign prostatic hypertrophy.

TABLE 1

Demographic Data

|  | Group One No statins | Group Two Used statins |
|---|---|---|
| Number (N): | 108 | 42 |
| Age (yrs) | 72.3 ± 4.4 | 72.2 ± 4.4 |
| Ever smoked | 83/106 (78.3%) | 27/42 (64.3%) |
| Current smoker | 14/108 (13.0%) | 3/42 (7.1%) |
| Diabetes Mellitus | 16/97 (16.5%) | 3/38 (7.9%) |
| History of M.I. | 16/108 (14.8%) | 13/42 (31%) |
| Hypertension | 46/106 (43.4%) | 18/41 (43.9%) |
| PSA ≦ 1.0 ug/L | 11/108 (10.2%) | 11/42 (26.2%) |

± = standard deviation

In the practice of the invention the medications may be administered as a tablet, or as a part of a liquid solution or dispersion, or patch or subcutaneous pellet in order to achieve systemic absorption of the drug. It should be understood that this invention will apply to the administration of the medications in any form for the purpose of systemic absorption for the purpose of treating, and preventing benign prostates hypertrophy. Such forms will include not only tablets, but also subcutaneous pellets or cutaneous patches or other forms resulting in systemic availability of the drug. The active ingredient can be administered as a liquid in the form of a solution or a dispersion using appropriate solvents and preservatives as well as adjusting the pH to the range of maximum stability. In the formulation of either solid or liquid pharmaceutically acceptable inactive ingredients may be used. These include excipients, preservatives or flavorings.

Without further elaboration the foregoing will so fully illustrate our invention that others, may, by applying current future knowledge, adopt the same for use under various conditions of service.

REFERENCES

1. Weisman K M, Larijani G E, Goldstein M R, and Goldberg M E. Relationship between benign prostatic hyperplasia and history of coronary artery disease in elderly men. Pharmacotherapy 2000:20(4);383–6
2. Hahn R G, Farahmand B Y, Hallin A, Hammer N, and Persson P G. Incidence of acute myocardial infarction and cause-specific mortality after transurethral treatments of prostatic hypertrophy. Urology 2000:55(2);236–240
3. Giovannucci E, Rimm E B, Chute C G, Kawachi I, Colditz G A, Stampfer M J, Willett W C. Obesity and benign prostatic hyperplasia. Am J Epidemiol 1994;140:989–1002.
4. Araki H, Waranabe H, Mishina T, Nakao M. High-risk group for benign prostatic hypertrophy. Prostate 1983; 4:253–264
5. Chyou P, Nomura A, Stemmermann G, Hamkin J. A prospective study of alcohol, diet and other lifestyle factors in relation to obstructive uropathy. The Prostate 1993; 22:253–264
6. Lagiou P, Wuu A, Trichopoulou C, Hsieh C-C, Adami H-O, Trichopolos D. Diet and benigh prostatic hyperplasia: A study in Greece. Urology 1999; 54:284–290
7. Rimm E B, Stampfer M J, Giovannucci E, Ascherio A, Spiegelman D, Colditz G A, Willet W C. Body size and fat distribution as predictors of coronary heart disease among middle-aged and older US men. Am J Epidemiol 1995;141:1117–27
8. Ulbricht T L V, Southgate D A T. Coronary heart disease: seven dietary factors. Lancet 1991; 338:985–992
9. McConell J D, Bruskewitz R., Walsh P, et al. The effect of Finasteride on the risk of acute urinary retention NEJM 1998;338:557
10. McNeal J E. Pathology of benign prostatic hyperplasia: insight into etiology. Urol Clin N Amer 1990;17:477–486
11. Hulley S, Grady D, Bush T, Ferburg C, Herrington D, Riggs B, Vittinghoff E. Randomized trial of estrogen plus progestin for secondary prevention of coronary heart disease in postmenopausal women. JAMA 1998;280:606–613
12. Downs J R, Clearfiled M, Weiss S, Whitney E, Shapiro D R, Beere P A, Langendorfer A, et al. Primary prevention of acute coronary events with lovastatin in men and women with average cholesterol levels. results of AFCAPS/TexCAPS. JAMA 1998;279:1615–22
13. Scandinavian Simvastatin Survival Study Group. Lancet 1994;344:1383–9
14. Berry M. Epidemiology of Prostatic Hyperplasia. 1997, AUA Update Series Vol XVI Lesson 35
15. Roehrborn C G, Boyle P, Gould A L, Waldstreicher J. Serum prostate-specific antigen as a predictor of prostate volume in men with benign prostatic hyperplasia. Urology 1999;53:581–589
16. Hochberg D A, Bassillotte J B, Frachia J A. Prostate specific antigen as a surrogate for prostate volume in patients with biopsy proven benign prostatic hyperplasia. J Urol 1999;161 (4supp):1113
17. Bosch R J, Griffiths D J, Blom J M, Schroeder F H. Treatment of benign prostatic hyperplasia by androgen deprivation: effects on prostate size and urodynamic parameters. J Urol 1989;141:68–7
18. Sech S M, Tingleaf C, Ahearns A Roehrborn C G. Longitudinal follow-up of serum prostate specific antigen levels following transurethral resection of the prostate for benign prostatic hyperplasia. J Urol 1999;161:4 (supp) 303

What is claimed is:

1. A method of treating or preventing benign prostatic hyperplasia and/or benign prostatic hypertrophy by administering to a person or an animal in need thereof, a pharmaceutically effective dose consisting of a HMG Co-A Reductase inhibitor.

2. A method of treating or preventing benign prostatic hyperplasia and/or benign prostatic hypertrophy by administering to a person or animal in need thereof, a pharmaceutically effective dose consisting of an HMG Co-A reductase inhibitor selected from the group:

fluvastatin sodium;

cerivastatin sodium;

atorvastatin calcium;

lovastatin;

provastatin sodium; and simvastatin.

3. The method in claim 2 wherein the effective amount of Fluvastatin sodium (Lescol) and dosing is 20 to 40 mg orally once daily.

4. The method in claim 2 wherein the effective amount of Cerivastatin sodium (Baycol) and dosing is 0.3 mg orally once daily.

5. The method in claim 2 wherein the effective amount of Atorvastatin Calcium (Lipitor) and dosing is 10 to 80 mg orally once daily.

6. The method in claim 2 wherein the effective amount of Lovastatin (Mevacor) and dosing is 10 to 80 mg orally once daily.

7. The method in claim 2 wherein the effective amount of Pravastatin sodium (Pravachol) and dosing is 10 to 40 mg orally once daily.

8. The method in claim 2 wherein the effective amount of Simvastatin (Zocor) and dosing is 5 to 80 mg orally once daily.

9. The invention of claim 2 wherein the active agent is administered as a tablet, or as a part of a liquid or solution or dispersion, or patch, or subcutaneous pellet, or intramuscular injection, or any other method with the intent of accomplishing systemic absorption of the drug.

\* \* \* \* \*